United States Patent
Biedermann et al.

(10) Patent No.: US 10,058,353 B2
(45) Date of Patent: Aug. 28, 2018

(54) BONE SCREW

(71) Applicant: Biedermann Technologies GmbH & Co. KG, Donaueschingen (DE)

(72) Inventors: Lutz Biedermann, VS-Villingen (DE); Jürgen Harms, Karlsruhe (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 15/299,189

(22) Filed: Oct. 20, 2016

(65) Prior Publication Data

US 2017/0164981 A1    Jun. 15, 2017

Related U.S. Application Data

(63) Continuation of application No. 14/488,730, filed on Sep. 17, 2014, now Pat. No. 9,498,256, which is a
(Continued)

(30) Foreign Application Priority Data

Nov. 10, 2000  (DE) .................................. 100 55 888
Dec. 27, 2000  (DE) .................................. 100 65 397

(51) Int. Cl.
*A61B 17/70*    (2006.01)
*A61B 17/86*    (2006.01)

(52) U.S. Cl.
CPC ...... *A61B 17/7032* (2013.01); *A61B 17/7037* (2013.01); *A61B 17/7038* (2013.01); *A61B 17/7067* (2013.01); *A61B 17/8605* (2013.01)

(58) Field of Classification Search
CPC .................. A61B 17/8605–17/866; A61B 17/7032–17/7046; A61B 17/7001; A61B 17/7067
(Continued)

(56) References Cited

U.S. PATENT DOCUMENTS

| | | |
|---|---|---|
| 4,484,570 A | 11/1984 | Sutter |
| 4,805,602 A | 2/1989 | Puno |
| (Continued) | | |

FOREIGN PATENT DOCUMENTS

| | | |
|---|---|---|
| CA | 2216955 | 2/2004 |
| DE | 19542116 A1 | 5/1997 |
| (Continued) | | |

OTHER PUBLICATIONS

Plaintiff Stryker Spine's Motion to Supplement the Record, filed Nov. 5, 2009, in Civil Action No. 08-1827-CKK, D.D.C. 8 pages.
(Continued)

*Primary Examiner* — Pedro Philogene
(74) *Attorney, Agent, or Firm* — Lewis Roca Rothgerber Christie LLP

(57) ABSTRACT

A bone screw having a screw member possessing a threaded section and a head and a receiving part at the head end for receiving a rod to be connected to the bone screw is provided. The receiving part has on open first bore and a substantially U-shaped cross-section having two free legs provided with a thread. Furthermore, the receiving part has a second bore on the end opposite to the first bore whose diameter is greater than that of the threaded section and smaller than that of the head. On the bottom of the first bore a seat for the head is provided. In order that the screw member can be pivoted to at least one side by an enlarged angle, the edge bounding the free end of the second bore viewed relative to the axis of the first bore is of asymmetric construction.

26 Claims, 1 Drawing Sheet

Related U.S. Application Data continuation of application No. 12/982,728, filed on Dec. 30, 2010, now Pat. No. 8,864,803, which is a continuation of application No. 11/319,427, filed on Dec. 29, 2005, now abandoned, which is a continuation of application No. 10/763,431, filed on Jan. 22, 2004, now Pat. No. 8,409,260, which is a continuation of application No. 10/037,698, filed on Nov. 9, 2001, now Pat. No. 6,736,820.

(58) Field of Classification Search
USPC .................................. 606/246–279, 300–328
See application file for complete search history.

(56) References Cited

U.S. PATENT DOCUMENTS

| | | |
|---|---|---|
| 4,946,458 A | 8/1990 | Harms |
| 5,057,111 A | 10/1991 | Park |
| 5,084,048 A | 1/1992 | Jacob |
| 5,129,388 A | 7/1992 | Vignaud |
| 5,133,717 A | 7/1992 | Chopin |
| 5,176,678 A | 1/1993 | Tsou |
| 5,190,543 A | 3/1993 | Schlapfer |
| 5,207,678 A | 5/1993 | Harms |
| 5,217,497 A | 6/1993 | Mehdian |
| 5,246,442 A | 9/1993 | Ashman |
| 5,253,406 A | 10/1993 | Shere |
| 5,344,422 A | 9/1994 | Frigg |
| 5,360,431 A | 11/1994 | Puno |
| 5,403,314 A | 4/1995 | Currier |
| 5,439,381 A | 8/1995 | Cohen |
| 5,443,467 A | 8/1995 | Biedermann |
| 5,466,237 A | 11/1995 | Byrd, III |
| 5,474,551 A | 12/1995 | Finn |
| 5,474,555 A | 12/1995 | Puno |
| 5,476,464 A | 12/1995 | Metz-Stavenhagen |
| 5,486,176 A | 1/1996 | Hildebrand et al. |
| 5,496,321 A | 3/1996 | Puno |
| 5,531,746 A | 7/1996 | Errico |
| 5,545,228 A * | 8/1996 | Kambin ............. A61B 17/7007 606/291 |
| 5,549,608 A | 8/1996 | Errico |
| 5,554,157 A | 9/1996 | Errico |
| 5,584,831 A | 12/1996 | McKay |
| 5,586,984 A | 12/1996 | Errico |
| 5,591,166 A | 1/1997 | Bernhardt |
| 5,609,593 A | 3/1997 | Errico |
| 5,647,873 A | 7/1997 | Errico |
| 5,669,911 A | 9/1997 | Errico |
| 5,672,176 A | 9/1997 | Biedermann |
| 5,690,630 A | 11/1997 | Errico |
| 5,725,527 A | 3/1998 | Biedermann |
| 5,725,528 A | 3/1998 | Errico |
| 5,728,098 A | 3/1998 | Sherman et al. |
| 5,733,285 A | 3/1998 | Errico |
| 5,733,286 A | 3/1998 | Errico |
| 5,735,850 A | 4/1998 | Baumgartner |
| 5,735,852 A | 4/1998 | Amrein |
| 5,752,957 A | 5/1998 | Ralph |
| 5,797,911 A | 8/1998 | Sherman |
| 5,810,818 A | 9/1998 | Errico |
| 5,873,878 A | 2/1999 | Harms |
| 5,879,350 A | 3/1999 | Sherman |
| 5,882,350 A | 3/1999 | Ralph |
| 5,885,286 A | 3/1999 | Sherman |
| 5,891,145 A | 4/1999 | Morrison et al. |
| 5,946,988 A | 9/1999 | Metz-Stavenhagen |
| 5,951,533 A | 9/1999 | Freeman |
| 5,954,725 A | 9/1999 | Sherman |
| 5,989,254 A | 11/1999 | Katz |
| 5,997,539 A | 12/1999 | Errico |
| 6,030,389 A | 2/2000 | Wagner |
| 6,053,917 A | 4/2000 | Sherman |
| 6,063,089 A | 5/2000 | Errico |
| 6,063,090 A | 5/2000 | Schlapfer |
| 6,074,391 A | 6/2000 | Metz-Stavenhagen |
| 6,077,262 A | 6/2000 | Schlapfer |
| 6,090,110 A | 7/2000 | Metz-Stavenhagen |
| 6,090,111 A | 7/2000 | Nichols |
| 6,113,601 A | 9/2000 | Tatar |
| 6,139,550 A | 10/2000 | Michelson |
| 6,280,442 B1 | 8/2001 | Barker |
| 6,296,642 B1 * | 10/2001 | Morrison ............ A61B 17/7032 606/300 |
| 6,299,614 B1 | 10/2001 | Kretschmer et al. |
| 6,325,802 B1 | 12/2001 | Frigg |
| 6,443,953 B1 | 9/2002 | Perra |
| 6,471,705 B1 | 10/2002 | Biedermann |
| 6,485,491 B1 | 11/2002 | Farris |
| 6,520,963 B1 | 2/2003 | McKinley |
| 6,554,834 B1 | 4/2003 | Crozet |
| 6,736,820 B2 | 5/2004 | Biedermann et al. |
| 6,755,830 B2 | 6/2004 | Minfelde et al. |
| 6,974,460 B2 | 12/2005 | Carbone et al. |
| 8,029,539 B2 * | 10/2011 | Kirschman ........ A61B 17/7032 606/246 |
| 8,480,714 B2 * | 7/2013 | Kirschman ........ A61B 17/7032 606/266 |
| 8,864,803 B2 | 10/2014 | Biedermann |
| 9,750,543 B2 * | 9/2017 | Biedermann ...... A61B 17/7037 |
| 2001/0034522 A1 | 10/2001 | Frigg |
| 2002/0091386 A1 | 7/2002 | Martin |
| 2002/0183748 A1 | 12/2002 | Martin |
| 2003/0045879 A1 | 3/2003 | Minfelde et al. |
| 2003/0055426 A1 | 3/2003 | Carbone |
| 2003/0171755 A1 * | 9/2003 | Moseley ............ A61B 17/7032 606/270 |
| 2004/0116929 A1 | 6/2004 | Barker et al. |
| 2004/0243126 A1 | 12/2004 | Carbone |
| 2005/0080420 A1 | 4/2005 | Farris |
| 2005/0283157 A1 | 12/2005 | Coates et al. |
| 2006/0058794 A1 | 3/2006 | Jackson |
| 2007/0265621 A1 | 11/2007 | Matthis et al. |
| 2008/0132953 A1 | 6/2008 | Carbone et al. |

FOREIGN PATENT DOCUMENTS

| | | |
|---|---|---|
| EP | 0582857 | 2/1994 |
| EP | 0885598 A2 | 12/1996 |
| EP | 1023873 A2 | 8/2000 |
| EP | 1090595 A2 | 9/2000 |
| EP | 1273270 A1 | 1/2003 |
| FR | 2802796 | 6/2001 |
| JP | 6-142115 A | 5/1994 |
| JP | 8-511189 | 11/1996 |
| WO | WO-88/03781 | 6/1988 |
| WO | WO-95/25474 | 9/1995 |
| WO | WO-98/34554 | 8/1998 |
| WO | WO-99/65415 | 6/1999 |
| WO | WO-01/6940 A1 | 7/2000 |
| WO | WO-01/58370 A1 | 1/2001 |
| WO | WO-01/47425 | 7/2001 |

OTHER PUBLICATIONS

Ninth Declaration of Natalie S. Morelli, dated Nov. 4, 2009, in Civil Action No. 08-1827-CKK, D.D.C. 13 pages.
Defendants' Opposition to Plaintiff's Motion to Supplement Record, filed Nov. 19, 2009, in Civil Action No. 08-1827-CKK, D.D.C. 3 pages.
Decision of Court on Motions for Summary Judgment dated Feb. 16, 2010, in Civil Action No. 08-1827-CKK, D.D.C. 56 pages.
Biedermann et al., U.S. Office action, dated Oct. 11, 2006, directed to U.S. Appl. No. 10/763,431; 19 pages.
Biedermann et al., U.S. Office Action, dated Dec. 11, 2007, directed to U.S. Appl. No. 11/291,920; 16 pages.
Biedermann et al., U.S. Office Action, dated Jun. 16, 2008, directed to U.S. Appl. No. 11/291,920; 6 pages.
Biedermann et al., U.S. Office Action, dated Jan. 12, 2009, directed to U.S. Appl. No. 11/291,920; 9 pages.
Biedermann et al., U.S. Office Action, dated Jul. 10, 2009, directed to U.S. Appl. No. 11/291,920; 6 pages.

(56) References Cited

OTHER PUBLICATIONS

Motion of Plaintiff Stryker Spine for Summary Judgment Regarding Defendant's Failure to Comply with 35 U.S.C. §112, filed on May 29, 2009; Civil Action No. 08-1827-CKK, 54 pages.
Motion of Plaintiff Stryker Spine for Summary Judgment Regarding Unpatentability of Defendants' Claims Under 35 U.S.C. §§ 102 and 103, filed on May 29, 2009; Civil Action No. 08-1827-CKK, 43 pages.
Defendant's Motion for Summary Judgment as to Each of Stryker Spine's Claims and Demand for Relief, filed on May 29, 2009; Case No. I:08-cv-1827-CKK, 87 pages.
Defendant's Reply in Support of Their Motion for Summary Judgment as to Each of Stryker Spine's Claims and Demands for Relief, filed on Jul. 6, 2009; Case No. 1:08-cv-1827-CKK, 58 pages.
Reply of Plaintiff Stryker Spine in Further Support of its Contingent Motion for Summary Judgment Regarding Defendant's Failure to Comply with 35 U.S.C. § 112, filed on Jul. 6, 2009; Case No. 1:08-cv-1827-CKK, 16 pages.
Reply of Plaintiff Stryker Spine in Further Support of Its Motion for Summary Judgment Regarding the PTO's Erroneous Refusal to Redefine the Interference "Count," filed on Jul. 6, 2009; Case No. 1:08-cv-1827-CKK, 30 pages.
Reply of Plaintiff Stryker Spine in Further Support of Its Contingent Motion for Summary Judgment or, in the Alternative, for Remand Regarding Unpatentability of Defendant's Claims Under 35 U.S.C. §§ 102 and 103, filed on Jul. 6, 2009; Civil Action No. 08-1827-CKK, 20 pages.
Letter from R. Wepner to B. Bretschneider and L. Dauchot dated Nov. 2, 2009, Regarding Civil Action No. 08-1827-CKK, D.D.C. 6 pages.
Expert Report of Dr. Bret Ferree in *Stryker Spine* v. *Biedermann Motech et al.*, Civil Action No. 1:08-cv-1827-CKK, D.D.C., Apr. 2, 2009.
Deposition of Dr. Bret Ferree in *Stryker Spine* v. *Biedermann Motech et al.*, Civil Action No. a:08-cv-1827-CKK, D.D.C., Apr. 30, 2009.
Japanese Notice of Grounds of Rejection dated Apr. 8, 2008, directed to JP Application No. 2001/343431, including translation.
Carbone's Response to European Office Action dated Dec. 20, 2005, directed to EP Application No. 02 292 236.3; 8 pages.
Carbone's Response to European Office Action dated Apr. 26, 2005, directed to EP Application No. 02 292 236.3; 9 pages.
European Office Action dated Dec. 20, 2005, directed to EP Application No. 02 292 236.3; 3 pages.
Office Action dated Apr. 8, 2004, from the European Patent Office in Carbone's counterpart application.
Office Action dated Jul. 1, 2004, issued in Carbone's U.S. Appl. No. 10/091,068.
Amendment filed on Aug. 11, 2004, in Carbone's U.S. Appl. No. 10/091,068.
European Office Action dated Apr. 26, 2005 relating to European Application No. 02 292 236.3-1265.

* cited by examiner

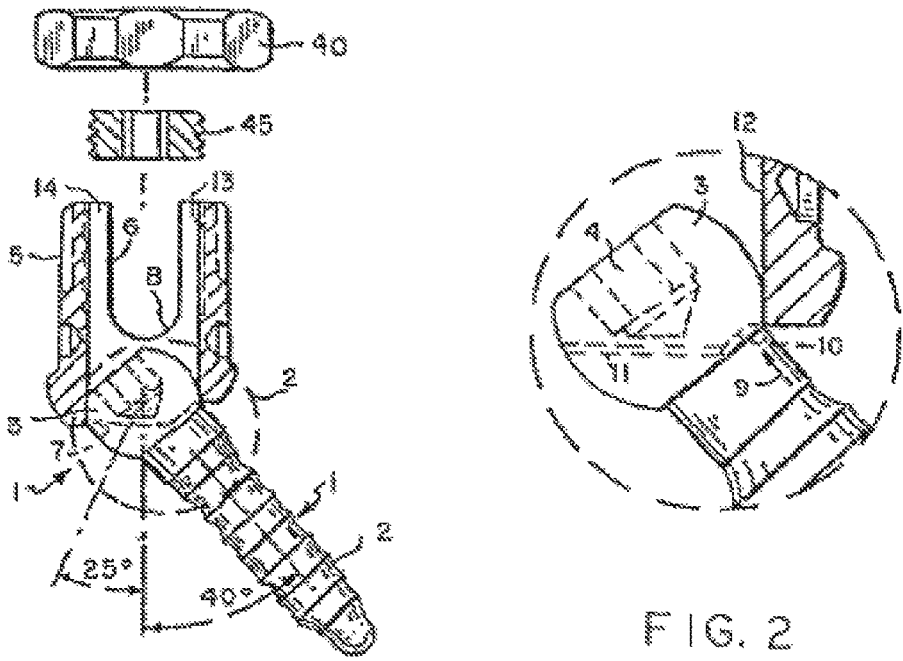
FIG. 1
FIG. 2
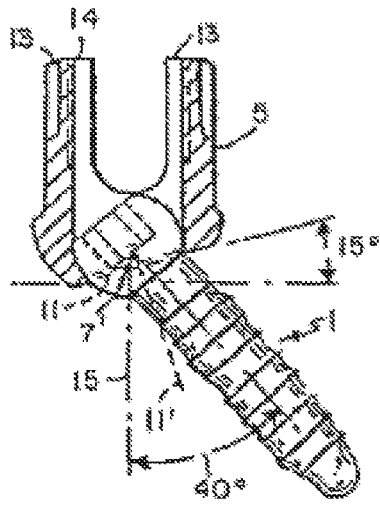
FIG. 3
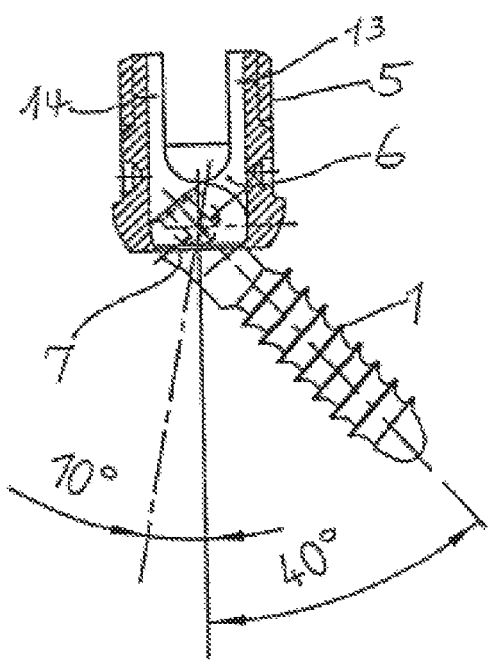
Fig. 4

BONE SCREW

CROSS-REFERENCE TO RELATED APPLICATIONS

This application is a continuation of U.S. application Ser. No. 14/488,730, filed Sep. 17, 2014, which is a continuation of U.S. application Ser. No. 12/982,728, filed Dec. 30, 2010, now U.S. Pat. No. 8,864,803, which is a continuation of U.S. application Ser. No. 11/319,427, filed Dec. 29, 2005 which is a continuation of U.S. application Ser. No. 10/763,431, filed Jan. 22, 2004, now U.S. Pat. No. 8,409,260, which is a continuation of U.S. application Ser. No. 10/037,698, filed Nov. 9, 2001, now U.S. Pat. No. 6,736,820, which claims the priority of German Patent Application No. 100 65 397.9, filed on Dec. 27, 2000 and German Patent Application No. 100 55 888.7, filed on Nov. 10, 2000, the disclosures of each of which are incorporated herein by reference.

FIELD AND BACKGROUND OF THE INVENTION

The invention relates to a bone screw having a threaded section and a head and a receiving part at the head end for receiving a rod to be connected to the bone screw, the receiving part possessing an open first bore and a substantially U-shaped cross-section having two free legs provided with a thread and a second bore at the end opposite to the first bore, whose diameter is greater than that of the threaded section and smaller than that of the head and which forms the seat for the head, and a nut or screw working together with the thread.

Such a bone screw is disclosed, for example, in U.S. Pat. No. 5,672,176. In the known bone screw the head is of spherical segment-shaped construction. The bottom of the first bore adjacent to the second bore is likewise of spherical segment-shaped construction so that the spherical head lies on this spherical section. The plane going through the bounding edge is oriented at right angles to the axis of the first bore and the mid-point of the second bore coincides with the axis of the first bore. By this means it is achieved that the threaded section possessing the head is pivotable in a predetermined angle of generally up to 25° about the axis of the first bore so that even after screwing the threaded section into a vertebral segment orientation of the receiving part receiving a rod is possible. At the same time, the size of the pivot angle is limited to the extent that the second bore as a function of the diameter of the head must not exceed d certain size so that the head still has an adequate hold in the receiving part.

The use of such bone screws is something of a problem in the region of cervical vertebrae. In this case, due to the small dimensions of the cervical vertebrae, it is necessary that the screws must always be pivoted to one side and upwards, a greater degree of pivoting being necessary than is the case in the larger thoracic vertebrae and lumbar vertebrae.

SUMMARY OF THE INVENTION

The aim of the invention is to provide a bone screw which permits a larger pivot angle. This task is solved by a bone screw having a screw member that possess a threaded section, a head and a receiving part at the head end for receiving a rod to be connected to the bone screw. The receiving part has an open first bore and a substantially U-shaped cross-section having two free legs provided with threads, a second bore at the end opposite the first bore having a diameter greater than the diameter of the threaded section and smaller than the diameter of the head, and a seat for the head and a nut or screw acting together with the thread. When viewed relative to the axis of the first bore, the edge bounding the free end of the second bore is asymmetrical.

Refinements of the invention are identified in the more detailed embodiments described below.

BRIEF DESCRIPTION OF THE DRAWINGS

Further features and practical advantages of the invention emerge from the description of exemplified embodiments with reference to the figures.

FIG. 1 depicts a side elevation of a first embodiment of the invention, partly in sectional representation.

FIG. 2 shows an enlarged detail of FIG. 1.

FIG. 3 depicts a side elevation, partly in sectional representation, of a second embodiment of the invention.

FIG. 4 depicts a corresponding representation of a further embodiment of the invention.

DETAILED DESCRIPTION OF THE INVENTION

The bone screw includes a screw member proper 1 having a threaded section 2 and a head 3. The head is formed in the shape of a segment of a sphere in the region adjoining the threaded section. Coaxial with the thread axis and on the end opposite to the threaded section 2 the head possesses a recess 4 for engagement with a socket screw key.

The bone screw further comprises a cylindrically constructed receiving part 5. At one end this has a first bore 6 of axially symmetrical construction. On the opposite end a second bore 7 is provided whose diameter is greater than that of the threaded section 2 and smaller than that of the head 3. On the end opposite to the second bore the first bore is open and its diameter is of such a size that that the screw member 1 can be guided through the open end by its threaded section 2 going through this bore and by the head going as far as the bottom of the first bore. The bottom of the first bore is constructed as a spherically shaped region towards the open end, the radius being substantially equal to the radius of the spherical segment-shaped section of the head 3. Furthermore, the receiving part 5 has a U-shaped recess 8 arranged symmetrically relative to the center of the part whose bottom is directed towards the second bore 7 and whose two side legs 13, 14 extend to the open end directed towards the first bore 6. At the free end of the legs 13, 14 a thread for engagement with a screw member constructed as a nut or screw is provided. The nut or screw serves to fax a rod to be inserted into the U-shaped recess 8, it being possible for the nut or screw to act on the rod directly or via a pressure member.

In the embodiment shown in FIGS. 1 and 2, in the direction of the arrow 9, whose direction lies in a plane going through the axis of symmetry of the first bore and which is inclined to the axis of symmetry by a predetermined angle, a circular countersink 10 is made in the edge between the opening plane 11 of the second bore and the edge 12 of the first bore.

In this manner, as can be seen in the figures, it is achieved that the angle between the axis of the screw member 1 and the axis of symmetry of the first bore is substantially enlarged by comparison with the angle otherwise attainable. At the same time the seat of the screw member 1 in the receiving part is retained.

In the second embodiment shown in FIG. 3 the interior of the receiving part 5 is constructed as in the first embodiment. The opening plane 11, which bounds the second bore 7, in this embodiment is inclined at a predetermined angle α to the plane bounded by the second bore 7 so that the normal to this plane 11 and the axis of symmetry of the first bore 15 enclose the angle of inclination. In the case shown this angle is 15° as an exemplified embodiment. In this version it is also achieved that the screw member 1 α pivotable in the direction shown by an angle to the axis of symmetry of the-first-bore which is substantially greater than the angle which is achievable in the usual mode of construction.

Both in the embodiment shown in FIG. 1 and the embodiment shown in FIG. 3 the countersink or chamfer is selected in such a way that in each case a small peripheral section still remains which still belongs to the spherical seat.

In a fourth embodiment which is not shown the mid-point of the second bore is constructed offset to the side to a small extent, for example by 0.5 mm, relative to the axis of symmetry of the first bore. This lateral offsetting in turn produces the result that the head is held in the mounting formed by the spherically constructed bottom but a greater pivot width is achieved in a side direction.

In the exemplified embodiments described above four different approaches to a solution are presented. It is also possible to combine the individual approaches with one another; that is, for example, to combine the solution according to the first and second exemplified embodiments or one of the two with the third and/or fourth exemplified embodiment, or even all four exemplified embodiments in order to achieve, in this way, a still greater possibility for pivoting in at least one direction.

In the exemplified embodiments described above the spherical bottom of the first bore 6 is constructed in each case as an integral component of the receiving part 5. In a modified embodiment, however, the spherical bottom can also be provided either in a mounting part introduced through the first bore 6 or in a mounting part introduced through the second bore 7. The invention is then used in a corresponding manner to the end that the receiving part together with the insert piece is regarded as one member and the measures described above are taken on this piece assembled in this way.

The members forming the bone screw are preferably made of titanium.

In the embodiment shown in FIG. 4 the edge bounding the free end of the second bore viewed relative to the axis of the first bore is of symmetrical construction. The asymmetry is achieved in that the screw 1 has a recess or countersink 16 on its neck engaging on the sphere or the spherical segment so that in the manner shown in FIG. 4 as in the exemplified embodiments previously described the enlarged pivot angle can be achieved.

What is claimed is:

1. A screw member of a pivotable bone screw, the screw member comprising:
    an elongate section having a first end, a second end, a longitudinal axis extending vertically through centers of the first and second ends, and an engagement structure on at least a portion thereof for engaging bone;
    a head comprising a spherical segment-shaped portion that is directed towards the elongate section; and
    a connecting region extending continuously from the spherical segment-shaped portion of the head to the engagement structure of the elongate section, wherein a horizontal width of the spherical segment-shaped portion is greater than a maximum outer width of the connecting region;
    wherein the second end of the elongate section is positioned between the first end of the elongate section and the head, and wherein at least a portion of the screw member that extends from the second end of the elongate section away from the first end of the elongate section is asymmetric with respect to the longitudinal axis.

2. The screw member of claim 1, wherein the engagement structure comprises a threaded section.

3. A bone screw comprising:
    the screw member of claim 1; and
    a receiving part comprising a seat for the head;
    wherein when the head is held in the seat, the receiving part is pivotable relative to the screw member such that an angle formed between the longitudinal axis of the elongate section of the screw member and a central axis of the receiving part is adjustable; and
    wherein the asymmetry of the screw member permits the screw member to pivot at a larger maximum angle in a first radial direction relative to the central axis of the receiving part than in a second radial direction relative to the central axis.

4. The screw member of claim 1, wherein the connecting region comprises a neck that connects the head with the second end of the elongate section, wherein the neck is asymmetric with respect to the longitudinal axis.

5. The screw member of claim 4, wherein at least a portion of the neck is recessed relative to other portions of the neck to form the asymmetry.

6. The screw member of claim 4, wherein a countersink is formed at the neck to form the asymmetry.

7. The screw member of claim 4, wherein the asymmetry of the neck engages the head.

8. The screw member of claim 4, wherein at least a portion of an outer surface of the neck is closer to the longitudinal axis in a first radial direction than in a second radial direction.

9. The screw member of claim 8, wherein the engagement structure comprises a threaded section, and wherein a distance between the longitudinal axis and the outer surface of the neck in the first radial direction is less than a distance between the longitudinal axis and a root of the threaded section.

10. The screw member of claim 9, wherein a distance between the longitudinal axis and the outer surface of the neck in the second radial direction is greater than the distance between the longitudinal axis and the root of the threaded section.

11. The screw member of claim 8, wherein the engagement structure comprises a threaded section, and wherein a distance between the longitudinal axis and the outer surface of the neck in the second radial direction is greater than a distance between the longitudinal axis and a root of the threaded section.

12. A bone screw comprising:
    a screw member comprising:
        an elongate section having a first end, a second end, a longitudinal axis extending through centers of the first and second ends, and an engagement structure on at least a portion thereof for engaging bone; and
        a head connected to the elongate section; and
    a receiving part having a seat for the head and a U-shaped cross-section for receiving a rod;

wherein when the head is held in the seat, the receiving part is pivotable relative to the screw member such that an angle formed between the longitudinal axis of the elongate section of the screw member and a central axis of the receiving part is adjustable; and wherein at least a portion of the screw member is asymmetric with respect to the longitudinal axis to permit the screw member to pivot at a larger maximum angle in a first radial direction relative to the central axis of the receiving part than in a second radial direction relative to the central axis.

13. The bone screw of claim 12, wherein the head comprises a spherical segment-shaped portion that is directed towards the elongate section.

14. The bone screw of claim 12, wherein the engagement structure comprises a threaded section.

15. The bone screw of claim 12, wherein the second end of the elongate section is positioned between the head and the first end of the elongate section, and wherein the bone screw further comprises a neck that connects the head with the second end of the elongate section, wherein the neck is asymmetric with respect to the longitudinal axis.

16. The bone screw of claim 15, wherein at least a portion of the neck is recessed relative to other portions of the neck to form the asymmetry.

17. The bone screw of claim 15, wherein a countersink is formed at the neck to form the asymmetry.

18. The bone screw of claim 15, wherein the asymmetry of the neck engages the head.

19. The bone screw of claim 15, wherein at least a portion of an outer surface of the neck is closer to the longitudinal axis in a first radial direction than in a second radial direction.

20. The bone screw of claim 19, wherein the engagement structure comprises a threaded section, and wherein a distance between the longitudinal axis and the outer surface of the neck in the first radial direction is less than a distance between the longitudinal axis and a root of the threaded section.

21. The bone screw of claim 20, wherein a distance between the longitudinal axis and the outer surface of the neck in the second radial direction is greater than the distance between the longitudinal axis and the root of the threaded section.

22. The bone screw of claim 19, wherein the engagement structure comprises a threaded section, and wherein a distance between the longitudinal axis and the outer surface of the neck in the second radial direction is greater than a distance between the longitudinal axis and a root of the threaded section.

23. A screw member of a pivotable bone screw, the screw member comprising:

an elongate section having a first end, a second end, and an engagement structure on at least a portion thereof for engaging bone; and a head, wherein the second end of the elongate section is positioned between the first end of the elongate section and the head, and wherein a longitudinal axis extends through centers of the first and second ends of the elongate section and through a center of the head;

wherein at least a portion of the screw member positioned between the second end of the elongate section and the center of the head is asymmetric with respect to the longitudinal axis.

24. The screw member of claim 23, further comprising a neck that connects the head with the second end of the elongate section, wherein the neck is asymmetric with respect to the longitudinal axis.

25. The screw member of claim 23, wherein the head comprises a spherical segment-shaped portion that is directed towards the elongate section.

26. A bone screw comprising:

the screw member of claim 23; and a receiving part comprising a seat for the head;

wherein when the head is held in the seat, the receiving part is pivotable relative to the screw member such that an angle formed between the longitudinal axis of the screw member and a central axis of the receiving part is adjustable; and wherein the asymmetry of the screw member permits the screw member to pivot at a larger maximum angle in a first radial direction relative to the central axis of the receiving part than in a second radial direction relative to the central axis.

* * * * *

UNITED STATES PATENT AND TRADEMARK OFFICE
CERTIFICATE OF CORRECTION

PATENT NO. : 10,058,353 B2
APPLICATION NO. : 15/299189
DATED : August 28, 2018
INVENTOR(S) : Lutz Biedermann et al.

Page 1 of 1

It is certified that error appears in the above-identified patent and that said Letters Patent is hereby corrected as shown below:

In the Specification
Column 2, Line 51        delete "fax" and insert -- fix --

Signed and Sealed this
Sixth Day of August, 2019

Andrei Iancu
*Director of the United States Patent and Trademark Office*